United States Patent [19]

Armstrong et al.

[11] Patent Number: 5,031,610

[45] Date of Patent: Jul. 16, 1991

[54] INHALATION DEVICE

[75] Inventors: John C. Armstrong, Milton; Richard C. J. Palson, Medfield, both of Mass.

[73] Assignee: Glaxo Inc., Research Triangle Park, N.C.

[21] Appl. No.: 183,499

[22] Filed: May 3, 1988

Related U.S. Application Data

[63] Continuation-in-part of Ser. No. 48,808, May 12, 1987, abandoned.

[51] Int. Cl.$^5$ .................................................. A61M 15/00
[52] U.S. Cl. ............................ 128/200.23; 128/203.15; 604/58
[58] Field of Search ...................... 128/200.23, 203.15; 604/58; 222/402.11–402.13, 402.2

[56] References Cited

U.S. PATENT DOCUMENTS

| | | |
|---|---|---|
| 3,157,179 | 11/1964 | Paullus et al. . |
| 3,456,645 | 7/1969 | Brock . |
| 3,456,646 | 7/1969 | Phillips et al. . |
| 3,598,294 | 8/1971 | Hedrick et al. . |
| 3,636,949 | 1/1972 | Kroop . |
| 3,789,843 | 2/1974 | Armstrong et al. . |
| 3,814,297 | 6/1974 | Warren . |
| 3,826,413 | 7/1974 | Warren . |
| 4,414,972 | 11/1983 | Young et al. . |
| 4,592,348 | 6/1986 | Waters et al. . |
| 4,648,393 | 3/1987 | Landis et al. . |
| 4,664,107 | 5/1987 | Wass . |
| 4,803,978 | 2/1989 | Johnson et al. . |

FOREIGN PATENT DOCUMENTS

3040641 5/1982 Fed. Rep. of Germany .
WO85/01880 5/1985 World Int. Prop. O. .

Primary Examiner—Randall L. Green
Assistant Examiner—K. M. Reichle
Attorney, Agent, or Firm—Darby & Darby

[57] ABSTRACT

A device for dispensing an aerosol from an aerosol module containing aerosol under pressure wherein there is a cocking device for readying it for release of the pressurized aerosol, a sear for retaining the cocking device in a non-operative position following readying and a vane operable by inhalation on the part of a user to disable the sear to thus release the cocking device to effect expulsion of aerosol from the aerosol module.

16 Claims, 6 Drawing Sheets

INHALATION DEVICE

RELATED APPLICATIONS

This application is a continuation-in-part of our previously filed application Ser. No. 48,808, filed May 12, 1987, entitled INHALATION DEVICE, now abandoned.

BACKGROUND OF THE INVENTION

There are a number of devices for dispensing aerosols for nasal and/or oral inhalation. Such devices are now quite well known for administering medicaments to patients suffering from bronchial conditions such as, for example, bronchial asthma. The most significant problem associated with such aerosols has been the difficulty for many patients to coordinate the release of the medicament with the initiation of the inspiratory effort. Many people, for example, elderly patients and children, find this synchronization difficult. These problems are alleviated with the breath-actuated devices such as the ones disclosed in U.S. Pat. Nos. 3,636,949; 3,789,843; 3,826,413; and WO85/01880. Sometimes these devices are also referred to as inhalation-oriented aerosols or, more simply, "demand valves". Simply, these devices eliminate the need for manual coordination by actuating automatically when the patient inhales with his lips in contact with the mouthpiece. Only light negative pressure is required to trip a simple mechanism which actuates the metering valve. The device must then be reset before the metering valve may discharge again. The instant application is concerned with a breath-actuated device of this type, but embodies improvements over the devices in the aforesaid patents in that it is structured to minimize the occasions of accidental discharge and, yet, discharge can be effected with minimum effort.

A long-standing problem with breath-actuated dispenser development has been the incompatability between the strong spring required to overcome the internal aerosol valve spring for effecting discharge, and the light pressure available to impaired individuals to trigger the device. The juncture between the two aforementioned elements in the past has been so tenuous that even the surface coefficient of friction of materials had to be considered. By the introduction of an intermediate sear element and other improvements to accomplish greater mechanical advantage, this invention achieves a positive yet sensitive latching and the degree of integrity required in medical dispensing devices.

SUMMARY OF THE INVENTION

As herein illustrated, the device is structured for use with an aerosol module and comprises a housing, a cradle disposed in the housing for receiving an aerosol module provided with a discharge stem movable from a disabling position to prevent discharge to an enabling position to permit discharge, the cradle being movable relative to the housing, a discharge nozzle member mounted in the housing in alignment with the discharge stem with which the discharge stem is engaged such that movement of the cradle relative to the nozzle effects movement of the stem relative to the module, a lever mounted in the housing operable to effect movement of the cradle relative to the nozzle member in a direction to enable the stem, to thus discharge a needed amount of aerosol formulation, spring means connected to the lever biasing the lever in a direction to enable the stem and means for constraining movement of said lever in said direction to enable the stem, comprising a sear disposed adjacent the distal end of the lever with which the distal end of the lever is engaged, a latch engaged with the sear holding the sear in the lever engaged position such that the stem is disabled, and means for disengaging the latch from the sear such as to permit the spring to move the lever to a position to enable the discharge stem. The lever is coupled to the cradle such that pivotal movement of the lever will on the one hand move the cradle in a direction to disable the stem and on the other hand move the cradle in a direction to enable the stem. There is cocking means coupled to the lever operable to move the lever in opposition to the spring means to a position to disable the stem and there is means for enabling the cocking means and for disabling the cocking means. The latch is pivotally supported at one end and has at its other end an arm accessible through an opening in the housing for manual displacement in a direction to disengage the latch from the sear in the event that the user has difficulty in initiating release by inspirational effort. The housing has an opening adjacent the nozzle member through which the aerosol ejected by engaging the valve can be projected and there is a closure member adapted to close the discharge opening and means connecting the closure member to the spring to hold the latter distended and the lever in a position such that the stem is disabled.

The invention will now be described with reference to the accompanying drawings, wherein:

FIGS. 8a and 8b are respectively an elevation and a plan view of the yoke used in the second embodiment. FIG. 8a showing also a portion of a strap attached thereto.

Referring to FIGS. 1 to 4 of the drawings, the device shown therein comprises a housing 10 defining chambers 12 and 14. A closure member 16 is hinged at one end by a pin 18 to one side of the chamber 12, the closure being provided at its opposite end with a latch element 20 interengageable with a latch element 22 on the housing.

Figure 1:
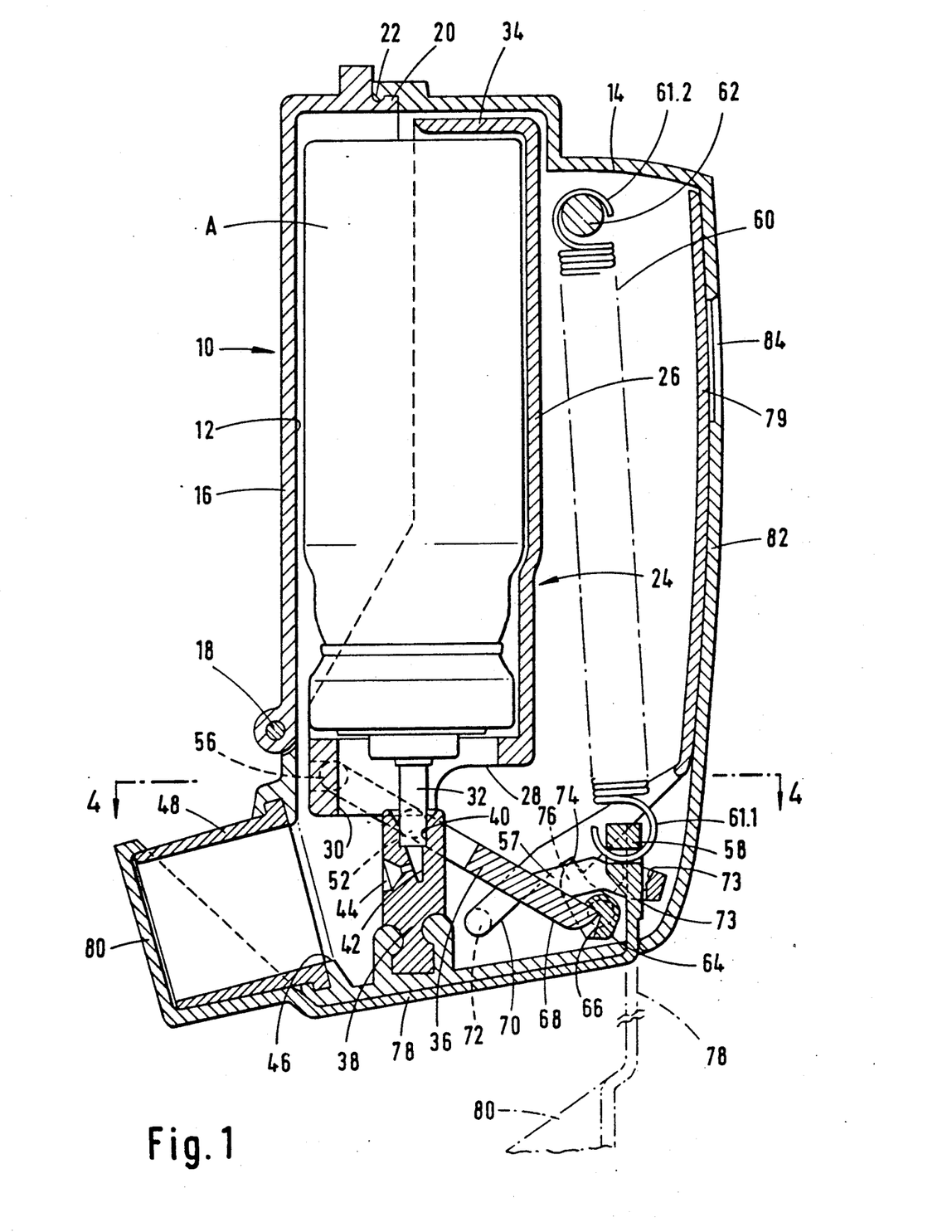
FIG. 1 is a vertical section of a first embodiment of the device, showing the components thereof in their inoperative position.

A cradle member 24 is mounted within the chamber 12 for vertical movement therein. The cradle 24 has semi-circular side wall 26 of a dimension and configuration corresponding substantially to the length and cross section of the aerosol module A to be disposed in the chamber and a bottom wall 28 containing a circular opening 30 for supporting the module in an inverted position within the chamber with its stem 32 extending through the bottom wall 28 into the chamber below the cradle. Desirably, the cradle 24 has at its upper end a capping element 34 for engagement with the bottom of the module to hold the module firmly engaged with the bottom 28. The cradle 24 is movable vertically within the housing 10 and there is means in the form of a yoke-shaped lever 36 operative in one position to hold the cradle 24 in an elevated position and in another position to hold it in a depressed position.

In that portion of the housing 10 below the cradle 24, there is mounted in a fixed position a nozzle member 38 containing an opening 40. The nozzle member 38 is disposed in alignment with the stem 32 for receiving the stem 32. The opening 40 is connected by a passage 42 to a discharge opening 44, the axis of which is concentrically centered with respect to an opening 46 formed in the lower part of the chamber 12 within which there is disposed an annular mouthpiece 48. As thus arranged, discharge from the aerosol module, as will appear hereinafter, is directed by the nozzle member 38 through the mouthpiece 48. Since the stem 32 remains stationary in the nozzle member 38 during operation, the desired disposal pattern is maintained at all times.

Discharge of aerosol from the module is effected by moving the cradle 24 downwardly relative to the nozzle member 38 to displace the stem 32 in the module. The aerosol module has a metering valve therin so that displacement of the stem 32 dispenses a dose of the material contained by the module through the nozzle element and directs it through the mouthpiece 48. After the dose has been dispensed no further material emerges from the stem until the stem has been first returned to its disabled position and then again put in its enabled position.

Figure 4:
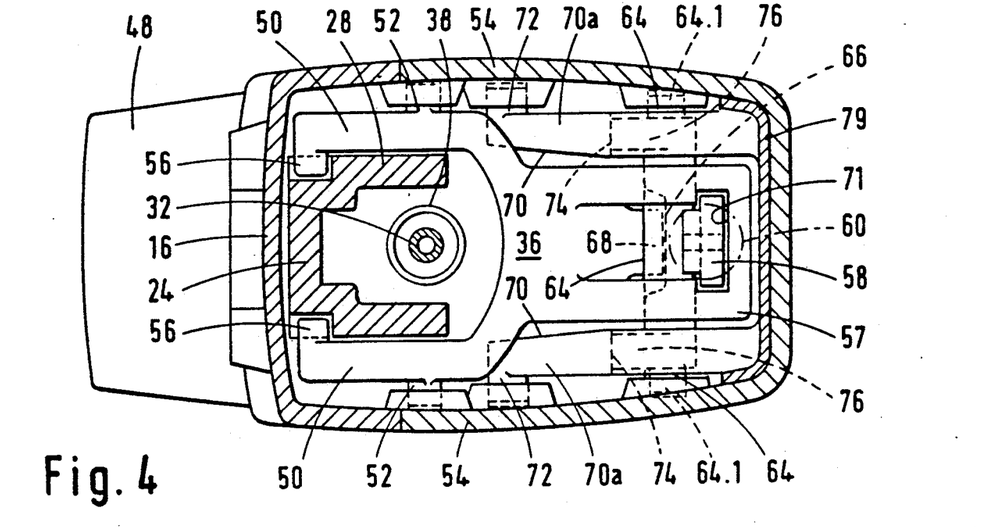
FIG. 4 is a transverse section taken on the line 4—4 of FIG. 1.

As herein illustrated, the yoke-shaped lever 36, FIG. 4, is provided with transversely spaced arms 50 each provided with a respective trunion 52 pivotally supported in the opposite side walls 54 of the housing for pivotal movement about a horizontal axis intermediate its opposite ends. At one end, the arms 50 of the yoke are pivotally connected by respective trunions 56 with the lower end of the cradle. At the opposite end, the lever 36 is connected by an arm 57 and coupling element 58 to the lower end 61.1 of a tension spring 60 mounted within the chamber 14. The arm 57 contains an opening 71 having oppositely diverging sides 73 through which the coupling element 58 extends. The upper end 61.2 of the spring 60 is connected to a pin 62 fixed between the walls of the chamber 14.

Within the lower end of the chamber 14, there is mounted a sear 64 which is rotatable about a horizontal axis parallel to the axis of rotation of the lever 36. The sear 64 extends across the chamber 14 from one side wall 54 to the other and is mounted for pivotal movement about the aforesaid horizontal axis by trunions 64.1 pivotally supported in the side walls 54. The sear 64 is provided in a central region thereof with a notch 66 of generally right angular section for engagement with the distal end portion 68 of the lever 36. The distal end position 68 and the notch 66 are sized and positioned so that the end portion 68 engages notch 66 immediately adjacent the pivot axis to minimize the forces on the lever 36 when the elements are engaged. The sear 64 is rotatable about its axis between one position in which it holds the distal end portion 68 of the lever 36 depressed (FIG. 1), in which position the opposite end of the lever holds the cradle 24 elevated and, hence, the stem 32 fully extended, and another position to release the distal end portion 68 of the lever 36 and allow the lever 36 to be elevated by the spring to a horizontal position (FIG. 3), such as to lower the cradle to a position to force the stem 32 into the module to cause aerosol discharge.

A latch member 70 having a pair of arms 70a is pivotally mounted at 72 to the side walls 54 for movement about a horizontal axis parallel to the axis of the sear. The latch 70 is provided adjacent its axially opposite ends with a pair of abutments 74 each of which is interengageable with a respective arm 76 integral with the sear.

In the inoperative position of the device, FIG. 1, the lever 36 is held in the depressed position by a cocking strap 78, one end of which is connected to the coupling 58 to which the spring 60 is attached and the other end of which has connected to it a cap 80 which fits over the end of the mouthpiece 48. When the cap 80 is fitted to the mouthpiece, the strap by way of the coupling 58 holds the spring 60 extended and the lever 36 in the depressed position with its distal end engaged with the sear 64. In this position, the latch member 70 is engaged with the arm 76. The latch member 70 has connected to its distal end an air vane 79 which, in the position of the latch as shown in FIG. 1, parallels the wall 82 of the chamber 14 and in this parallel position, covers an opening 84 in the wall. In the non-operative position of the device, the cap 80 is engaged with the mouthpiece 48, the air vane is engaged with the wall 82 so as to cover the opening 84 and the linkage is held in the position shown in FIG. 1 by the spring 60 so that the stem 32 is fully extended, that is, in the shut off position.

Figure 2:
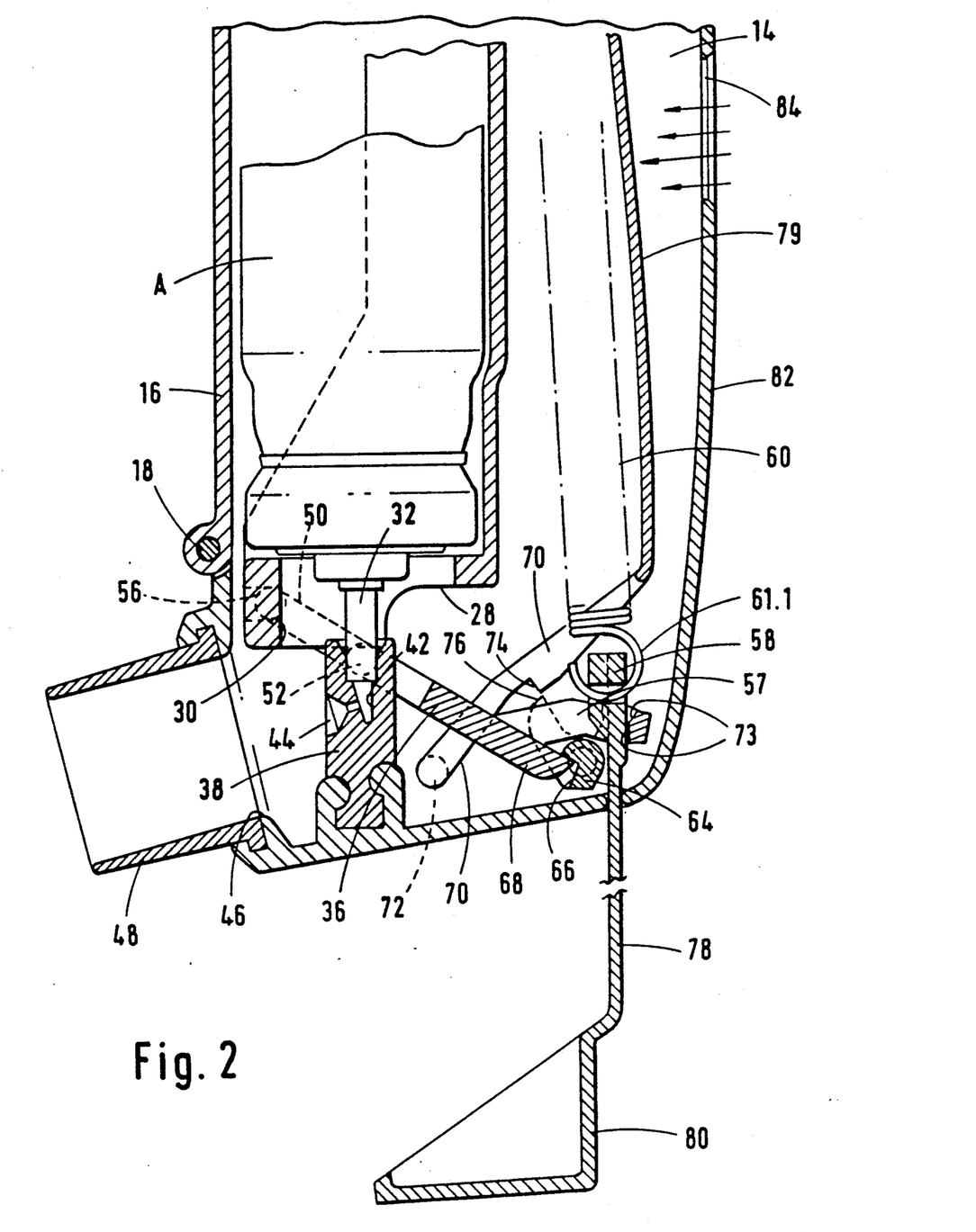
FIG. 2 is a vertical section of the device of FIG. 1 showing the componets thereof in a position preparatory to use.
Figure 3:
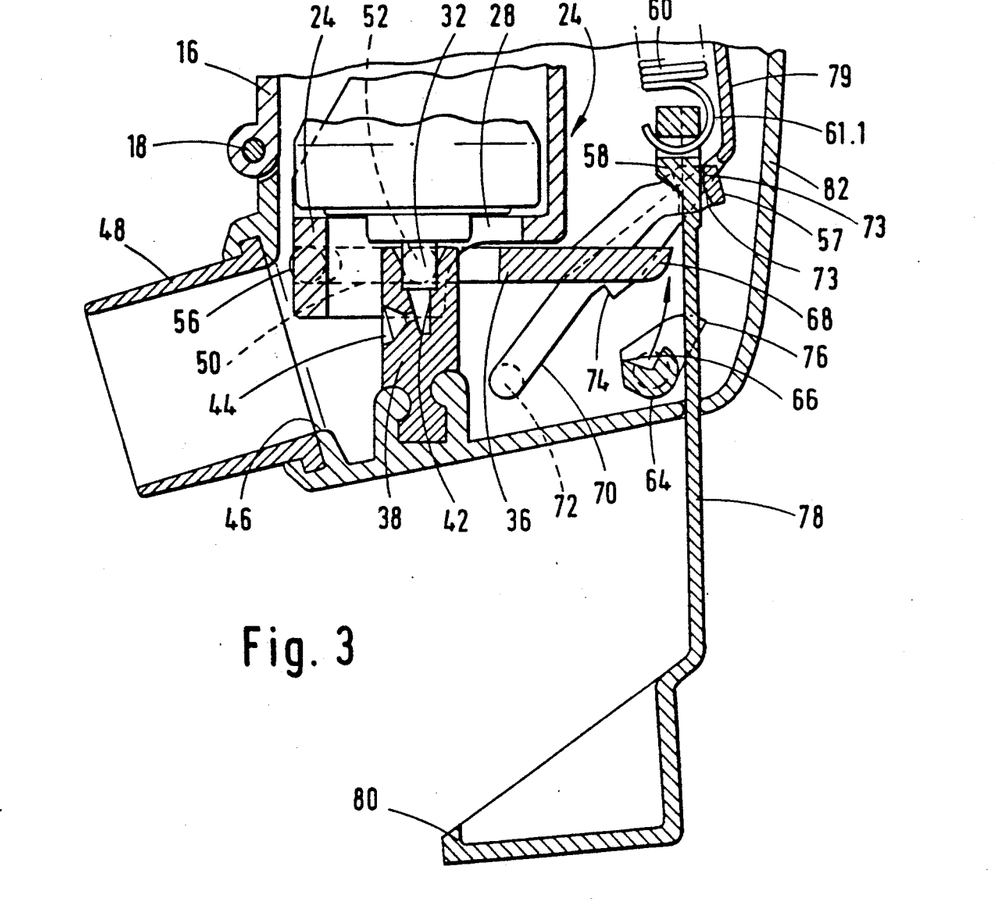
FIG. 3 is a vertical section of the device of FIG. 1 showing the components in their operative position.

To ready the device for use, the cap 80 is disengaged from the mouthpiece 48, FIG. 2. Disengagement of the cap allows the strap 78 to free the distal end of the arm 57 so that the distal end of the lever 36 is held depressed only by virtue of the fact that the lever 36 cannot move without its distal end portion 68 rotating the sear, and the sear cannot rotate because of the engagement of the arms 76 with the abutments 74 of the latch member 70. With the cap 80 removed, the device is ready for use. When the user inhales through the mouthpiece 48, thus lowering the pressure in the chamber 14, the air vane 79 swings from its position of engagement with the wall 82 toward the left, as illustrated in FIG. 3. Movement of the air vane 79 to the left disengages the abutments 74 of the latch member 70 from the arm 76, thus freeing the sear 64 to rotate. The spring 60 is thus able to pull the right hand end of the lever 36 upwardly. Since the lever 36 is mounted for pivotal movement with respect to the housing by the trunions 52 this causes the left hand end of the lever 36 to move downwardly carrying the cradle 24 with it. Downward movement of the cradle 24 displaces the stem 32 into the module which effects discharge of aerosol from the module through the nozzle and mouthpiece. When the aspiration is discontinued, the air vane assumes its closed position under the influence of gravity.

After inhalation the user grips the cap 80 and pulls downwardly on it against the force exerted via the strap 78 by the spring 60. The user is then able to re-engage the cap 80 on the mouthpiece 48. The device is thus restored to the position shown in FIG. 1. It will be observed that this involved, inter alia, the restoration of the lever 36, sear 64 and the latch member 70 to the positions of FIG. 1, and the way in which this occurs will now be described briefly. As the cap and strap are pulled down the lever 36 pivots about the trunions 52 in a clockwise direction as viewed in FIGS. 1 to 3, and a point is reached where the distal end portion 68 comes into contact with the notch 66 in the central region of the sear 64. As downward movement of the cap and strap continues the engagement between the distal end portion 68 and the notch 66 causes the sear 64 to pivot in a counterclockwise direction. In the course of this counterclockwise pivoting movement the arms 76 strike the undersides of the respective latch member arms 70a and the latch member 70 is thus caused to pivot counterclockwise through a small angle to allow the arms 76 to pass. Once the arms 76 are past the respective abutments 74 the latch member 70 is free to fall into the position shown in FIG. 1 under the influence of gravity, with the arms 76 each engaged behind a respective abutment 74. At this point the configuration shown in FIG. 1 is attained.

The embodiment shown in FIGS. 5 to 9 is similar in many respects to the embodiment shown in FIGS. 1 to 4, and will therefore not be described in detail. Elements in the embodiment of FIGS. 5 to 9 which correspond broadly to elements in the embodiment of FIGS. 1 to 4 are denoted by the same reference numerals but with the addition of 100. Attention will now be drawn to the more significant of the aspects in which the embodiment of FIGS. 5 to 9 differs from the embodiment of FIGS. 1 to 4.

Figure 5:
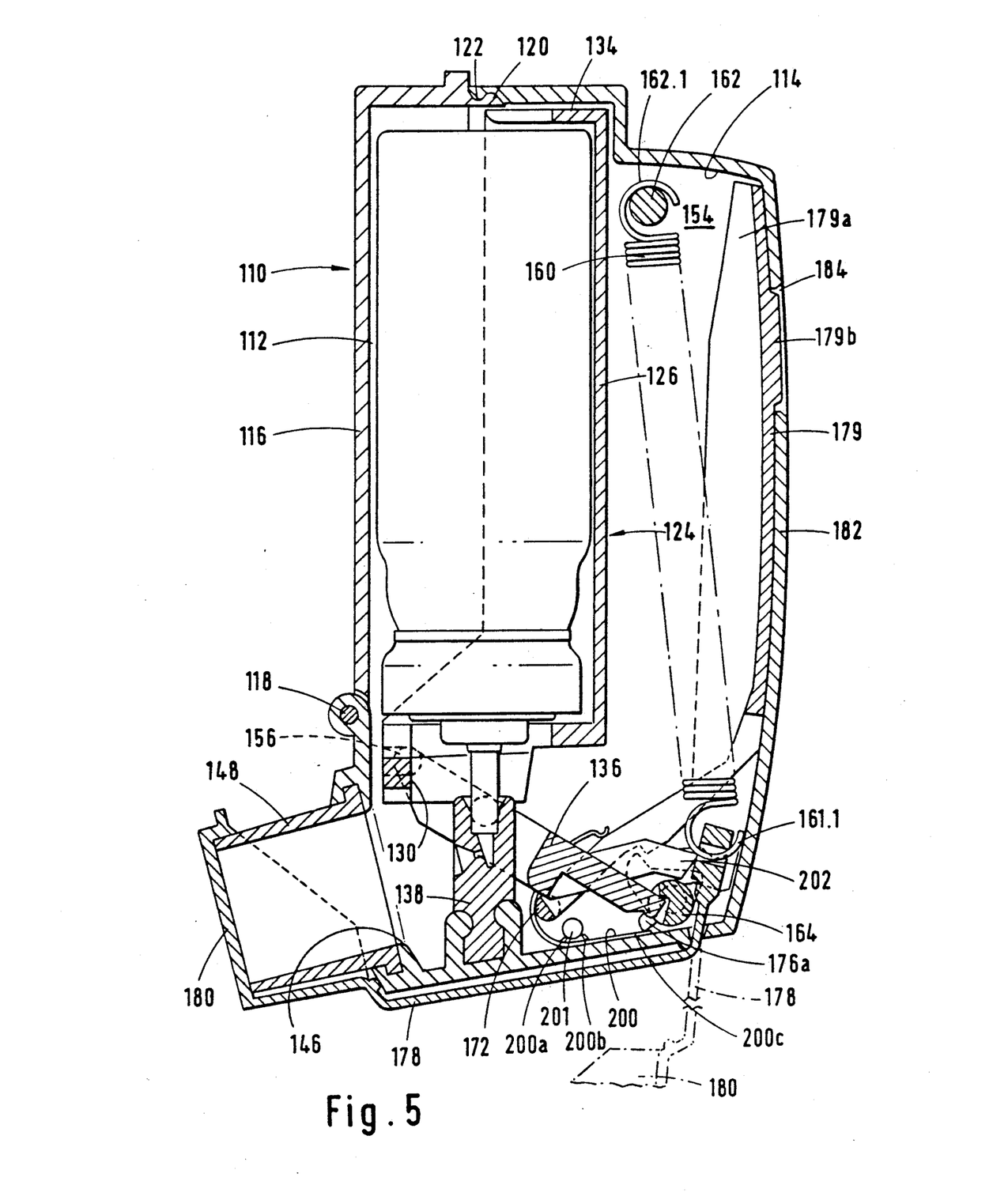
FIGS. 5 to 7 are views corresponding to FIGS. 1 to 3 respectively of a second embodiment.

Attention is directed firstly to the construction of the sear 164. For convenience this is shown on an enlarged scale in perspective in FIG. 9. It will be seen that each of the arms 176 has a protrusion 176a which extends approximately radiacally in a direction generally at right angles to the direction in which the main body of the arm 176 extends. As can be seen in FIG. 5, when the device is its inoperative position one of these protrusions 176a bears against a flat spring 200 which is of generally U-shape and which is secured intermediate its ends to the bottom of the housing. The spring 200 extends about a pin 201 extending laterally from one of the side walls 154 of the housing. The spring includes upwardly bent portions 200a and 200b located on opposite sides of the pin which serve to position the spring relative to the pin. The extension 200 of the spring is inclined upwardly and is depressed by the protrusion 176a when the elements are in the position shown in FIG. 5. Accordingly, the flat spring biases the sear in the clockwise direction. No second strip spring need be provided on the other side of the device, and the other protrusion 176a is therefore, strictly speaking, unnecessary. The protrusions 176a serve firstly to prevent the sear from rotating too far counterclockwise as viewed in FIGS. 5 to 7. In the absence of the protrusions the sear might rotate so far that the notch 166 would not be in a position to be engaged by the distal end portion 168 of the lever 136 during the procedure of restoring the device to its initial inoperative condition after inhalation (i.e. restoring it to the condition shown in FIG. 5). The presence of the protrusions 176a and the clockwise bias of the spring 200 acting on the protrusion 176a ensures that the notch 166 is in the correct position after inhalation for engagement by the distal end portion 168.

Figure 9A:
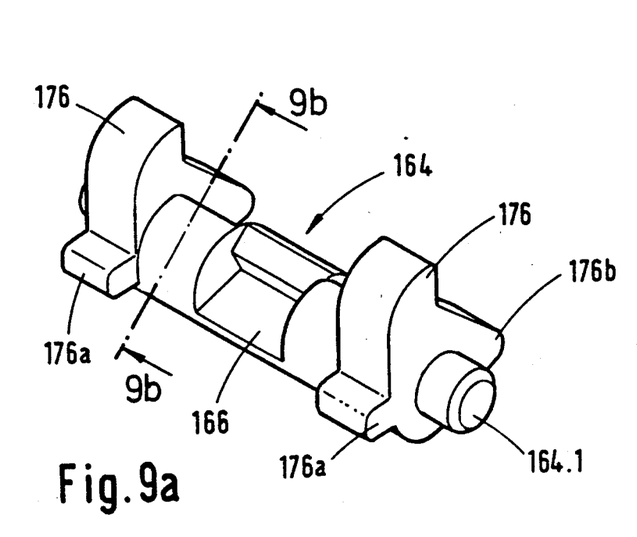
FIGS. 9a and 9b are respectively a perspective view and a cross-section taken along line 9b—9b of FIG. 9a of the sear used in the second embodiment.
Figure 9B:
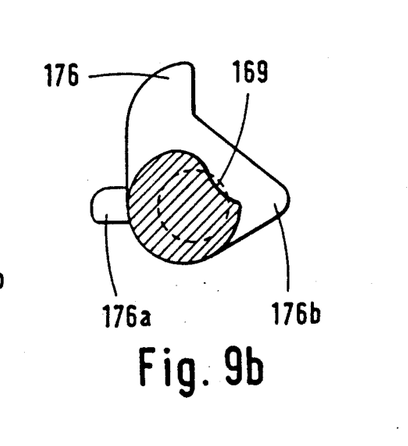

The protrusion 176a which engages the spring 200 has a light force exerted thereon by the spring, and this provides an additional impetus to the sear to ensure its clockwise rotation when inhalation takes place, over and above the force exerted on the notch 166 by the distal end portion 168 of the lever 136.

It will also be seen from FIG. 9 that on the opposite side of the arm 176 to the protrusion 176a is a further protrusion 176b. As can be appreciated by considering, for example FIG. 7, the protrusions 176b prevent excessive rotation of the sear in a clockwise direction by abutting the bottom wall of the housing.

One further aspect of the sear which should be noted is that the regions of the sear immediately on either side of the notch 166 are provided with recesses 169. During the initial stage of returning the device after inhalation to the state of FIG. 5 rotation of the sear in a counterclockwise direction is accomplished by engagement between the distal end portion 168 of the lever 136 and the notch 166. However, the final portion of this counterclockwise rotation is accomplished by engagement between cam surfaces 204 on the lever 136 and the recesses 169. At this point it may be convenient to note that the yoke 136 differs somewhat from the yoke 36 used in the first embodiment. In particular, the arm 57 is absent, so that there extends rearwardly from the main portion of the lever 136 a pair of arms 202 which are not connected at their rearward ends. The upper portion of the strap has a section of reduced width and increased thickness 178a between the arms 202, and sections of full width and increased section immediately above and below the arms. The section above the arms is concave and is received in a pair of convex recesses 203, one formed in each of the arms 202.

Figure 6:
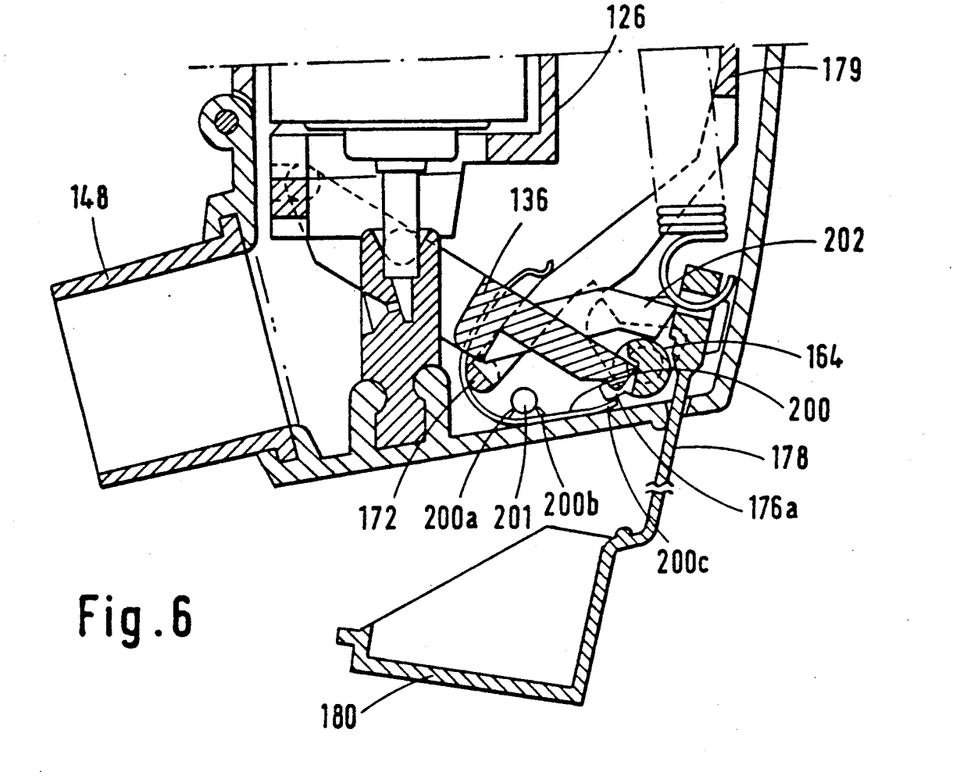
Figure 7:
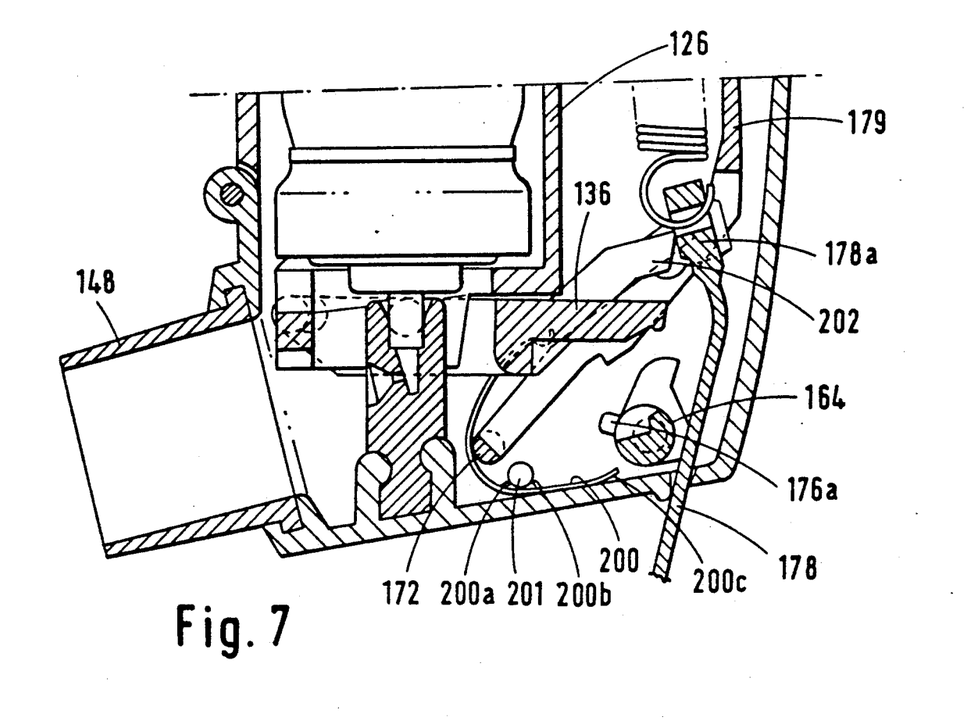
Figure 8A:
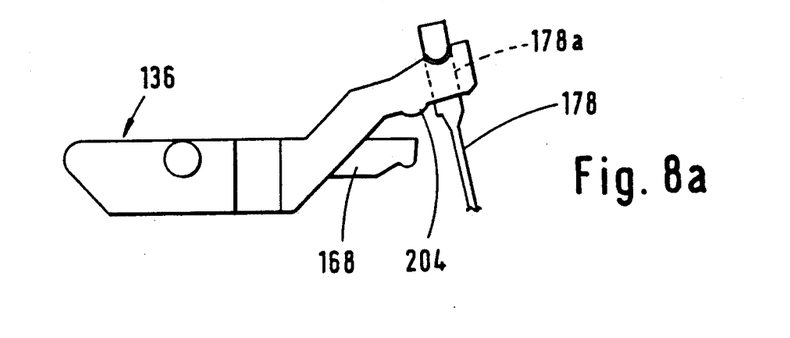
Figure 8B:
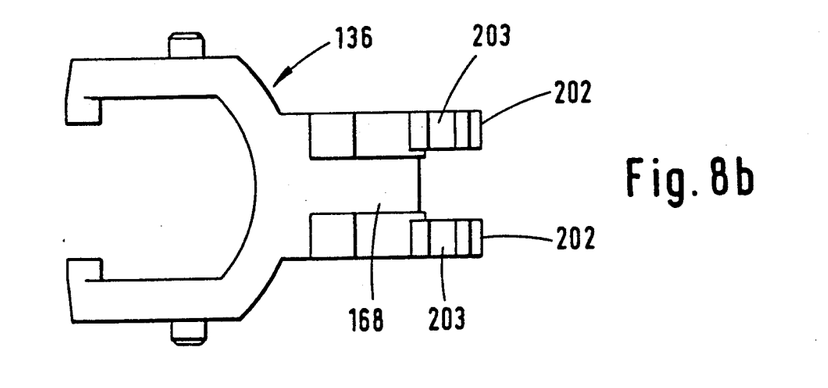

The U-shaped spring 200 serves a purpose in addition to exerting a force on one of the protrusions 176a. As can be seen in FIGS. 5 to 7 the upper portion of the spring bears on one of the arms 70a of the latch member 70. This helps to ensure that after the cap 180 has been removed from the nozzle 48, as indicated in FIG. 6, the latch member 70 cannot become accidentally disengaged from the arms 76, and that disengagement will only take place when the user inhales. The presence of the spring 200 means that a slight additional force has to be exerted through inhalation in order to disengage the latch member from the arms 76, but this additional force is slight, provided the spring 200 is chosen to be appropriately weak. Furthermore, the effect of the spring 200 in requiring an additional force is more than counterbalanced by an improvement in the design of the air vane of the embodiment of FIGS. 5 to 9, over and above the air vane used in the embodiment of FIGS. 1 to 4. As can be seen in FIG. 5, the air vane 179 is provided with side walls 179a which extend forwardly from the main portion of the air vane and approximately perpendicular thereto. The side walls are each close to a respective side wall 154, and their presence helps to ensure that the suction force produced when a patient inhales is highly effective in producing a force on the air vane. The main portion of the air vane 179 has a button 179b which, in the position shown in FIG. 5, is received in the opening 184. The main purpose of this is to provide a button which is clearly identifiable to a user as being such. It should be mentioned at this point that if a user desires to do so he can, instead of operating the device automatically by inhalation, operate it by pressing the button 179b and thereby causing the air vane 179 to move inwardly as it would have done had the patient caused it to move by inhalation.

It should be understood that the present disclosure is for the purpose of illustration only and includes all modifications or improvements which fall within the scope of the appended claims.

What is claimed is:

1. A dispensing device for use with an aerosol module having a body portion and a discharge stem extending from said body portion and movable with respect to the body portion from a disabling position in which it prevents discharge of the contents of the module to an enabling position in which it permits discharge, the device comprising:

(a) a housing, (b) a cradle movably supported in the housing, said cradle having a recess therein for receiving the aerosol module in said recess, and an opening wherethrough the stem of a module when received in said device will protrude, (c) a discharge nozzle member mounted in the housing in spaced relationship to the cradle and having a stem receiving portion therein for receiving the protruding discharge stem of a module when a module is received in said dispensing device, (d) moving means within said housing for movement of said cradle toward and away from said discharge nozzle member, movement of the cradle toward the discharge nozzle member effecting movement relative to said module body portion of the stem to its enabling position when a module is received in said dispensing device, (e) said moving means comprising a lever of length movably mounted to said housing at a first position along said length and connected to said cradle at a second position along said length to effect movement of the cradle relative to the housing in response to movement of said lever relative to said housing, (f) spring means connected to the lever for biasing the lever in a direction to enable the stem, (g) restraining means for restraining movement of said lever in said enabling direction, said restraining means comprising sear means mounted on said housing for relative movement into engagement with said lever, and latch means mounted on said housing for relative movement into engagement with said sear means for maintaining said sear means in the lever-engaged position to prevent movement of the lever and thereby movement of the cradle to the stem enabling position; and (h) means for disengaging the latch means from the sear means so as to permit the spring means to move the lever to a position to enable the discharge stem when a module is received in the dispensing device.

2. A device according to claim 1, wherein the lever is pivotably mounted at said first position intermediate its ends to the housing for pivotal movement about an axis, and has said second position thereof pivotably connected to said cradle and an end thereof away from said cradle disposed for movement into engagement with the sear means.

3. A device according to claim 2, wherein the sear means is mounted adjacent to said lever for pivotal movement about an axis parallel to the axis of pivotal movement of the lever and said sear means includes a notch therein, and wherein said end of the lever engages the sear means in said notch immediately adjacent the pivotal axis of the sear means when said lever is pivoted in one direction relative to said housing, said engagement causing said sear means to rotate about its axis to a position enabling said latch means to engage said sear means.

4. A device according to claim 1, comprising cocking means coupled to the lever and operable to move the lever in opposition to the spring means to a position to disable the stem.

5. A device according to claim 4, comprising means for enabling the cocking means and for disabling the cocking means.

6. A device according to claim 5, wherein the housing has an opening in communication with said cradle opening and with said discharge nozzle member through which aerosol ejected by enabling the valve stem is projected, and wherein the enabling and disabling means comprises a closure adapted to releasably cover said opening, said closure being attached to the cocking means, said cocking means being coupled to said lever, said lever being fixed in position when said closure covers said opening.

7. A device according to claim 6, wherein the cocking means is a flexible strap.

8. A device according to claim 1, wherein said housing has an opening therein, and the latch means has ends, said latch means being pivotably supported on said housing at one end and has at its other end an arm means accessible through said opening in the housing, said latch means being subject to manual displacement by a force applied through said opening to said arm means in a direction to disengage the latch means from the sear means.

9. A device according to claim 1, wherein the latch means is pivotably supported on said housing at one end and has at its other end an air vane disposed within the housing, and the housing contains at least one opening, said air vane means covering said at least one opening when the latch means is engaged by the sear means and displaceable in a direction to disengage the sear means when a reduced pressure inside the housing as compared to outside is created.

10. A device according to claim 9, comprising additional spring means for biasing the latch means into its opening-covering position.

11. A device according to claim 1, wherein the sear means is pivotally mounted to the housing for pivotal movement between an operative, latch means engaging position and an inoperative position.

12. A device according to claim 11, wherein the sear means is mounted adjacent said lever, and said lever has a surface portion arranged to engage a cooperating surface portion of the sear means, said engagement urging the sear means to pivot in a given direction when said lever pivots, said latch means comprising a member having a surface portion positioned in the path of movement of said sear means, whereby said sear means is subject to movement into its latchengaging position relative to said latch means under the influence of a force exerted on the lever.

13. A device according to claim 12, wherein the said cooperating surface portions are operative during disengagement of the latch means from the sear means to cause the sear means to pivot further in said given direction into its inoperative position.

14. A device according to claim 13, comprising auxiliary spring means for assisting the said further pivoting.

15. A device according to claim 12, which comprises cocking means coupled to the lever and operable to move the lever in opposition to the spring means to produce a position of said cradle to disable the stem, and wherein the said cooperating portions of the sear means and the lever are operative, upon such movement, to pivot the sear means in a direction opposite the said given direction to return said sear means to its latch-engaging position.

16. A device according to claim 11, wherein the sear means is provided with means preventing pivotal movement outside a predetermined range.

* * * * *